US008845577B2

(12) United States Patent
Cox

(10) Patent No.: US 8,845,577 B2
(45) Date of Patent: Sep. 30, 2014

(54) ENEMA DISPENSER

(75) Inventor: Charles H. Cox, Concord, VA (US)

(73) Assignee: C.B. Fleet Company, Inc., Lynchburg, VA (US)

(*) Notice: Subject to any disclaimer, the term of this patent is extended or adjusted under 35 U.S.C. 154(b) by 0 days.

(21) Appl. No.: 13/410,972

(22) Filed: Mar. 2, 2012

(65) Prior Publication Data

US 2012/0191045 A1 Jul. 26, 2012

Related U.S. Application Data

(63) Continuation of application No. 11/152,818, filed on Jun. 14, 2005, now Pat. No. 8,147,445.

(51) Int. Cl.
*A61M 5/178* (2006.01)
*A61M 39/22* (2006.01)
*A61M 3/02* (2006.01)

(52) U.S. Cl.
CPC ........... *A61M 3/0262* (2013.01); *A61M 39/221* (2013.01); *A61M 3/0279* (2013.01)
USPC ............. 604/37; 604/132; 604/275; 604/911; 604/19; 604/257

(58) Field of Classification Search
USPC ......... 604/275, 257, 19, 27, 212, 279, 36, 37, 604/911, 99.03, 132, 167.04; 137/849; 222/20
See application file for complete search history.

(56) References Cited

U.S. PATENT DOCUMENTS

| | | | |
|---|---|---|---|
| 2,869,545 A * | 1/1959 | Forsyth | 604/192 |
| 3,507,280 A | 4/1970 | Pollock | |
| 4,068,663 A | 1/1978 | D'Alessandro | |
| 4,133,457 A * | 1/1979 | Klassen | 222/212 |
| 4,211,777 A | 7/1980 | Chambers | |
| 4,226,342 A | 10/1980 | Laauwe | |
| 4,314,658 A * | 2/1982 | Laauwe | 222/213 |
| 4,619,645 A | 10/1986 | Hussey | |
| 4,728,006 A | 3/1988 | Drobish et al. | |
| RE33,239 E | 6/1990 | Halskov | |
| 5,219,573 A | 6/1993 | Tarka, Jr. et al. | |

(Continued)

FOREIGN PATENT DOCUMENTS

| | | |
|---|---|---|
| JP | 2003/190298 | 7/2003 |
| WO | 85/04108 | 9/1985 |
| WO | 2006/138076 | 12/2006 |

OTHER PUBLICATIONS

Enema Casen 80 mL product packing, Laboratorios Casen-Fleet, S.A., (2005).

(Continued)

*Primary Examiner* — Kevin C Sirmons
*Assistant Examiner* — Deanna K Hall
(74) *Attorney, Agent, or Firm* — Evan Law Group LLC

(57) ABSTRACT

An enema includes a liquid in a dispenser having a bottle, a nozzle attached to the bottle, and a valve. The valve may be a membrane having a slit and a thickness of at most 0.90 mm. The valve may be attached to the bottle or it may be attached to the nozzle. The enema can be administered more easily, with a lower amount of force. A method of bowel cleansing includes inserting the enema into a rectum and applying a compression force to the enema bottle.

21 Claims, 12 Drawing Sheets

(56) References Cited

U.S. PATENT DOCUMENTS

| | | | |
|---|---|---|---|
| 5,304,155 | A | 4/1994 | Lui |
| 5,680,969 | A | 10/1997 | Gross |
| 5,794,661 | A | 8/1998 | Natalizia |
| 6,103,268 | A | 8/2000 | Borody et al. |
| 6,110,150 | A | 8/2000 | Singo et al. |
| 6,416,499 | B2 | 7/2002 | Paul, Jr. |
| 6,461,324 | B1 | 10/2002 | Schlensog |
| 6,712,791 | B2 | 3/2004 | Lui et al. |
| 8,147,445 | B2 | 4/2012 | Cox |
| 2004/0009236 | A1 | 1/2004 | Halow |
| 2005/0027261 | A1 | 2/2005 | Weaver et al. |
| 2005/0049555 | A1 | 3/2005 | Moorehead et al. |
| 2005/0255170 | A1 | 11/2005 | Post et al. |
| 2007/0005025 | A1 | 1/2007 | Cox |
| 2007/0166181 | A1 | 7/2007 | Nilson |
| 2011/0066117 | A1 | 3/2011 | Post |

OTHER PUBLICATIONS

Enema Casen 140 mL, product packing, Laboratorios Casen-Fleet, S.A., (2006).

Enema Casen 250 mL, product packing, Laboratorios Casen-Fleet, S.A., (2003).

Fleet Enema, 4.5 Fl oz (133mL), product packaging, C.B. Fleet Co., Lynchburg, VA, © (1999).

Fleet Enema Extra, 7.8 oz (230 mL), product packaging, C.B. Fleet Co., Lynchburg, VA, © (2003).

International Search Report dated Oct. 6, 2006 for PCT application No. PCT/US2006/021368, 15 Pages.

Product Description of "Nitrile (Buna-N) Sheet Rubber", Chemical Identification: butadiene acrylonitrile, Buna-N, NBR, J. W. Industries, http://www.jwindustries.thomasregister.com/olc/33727371/page4.htm, 3 pages, (2005).

Edgren, C.S., et al., "Grip force vectors for varying handle diameters and hand sizes", Human Factors, vol. 46, No. 2, pp. 244-251, (2004).

Casey, J.S., et al., "Getting a grip on grip force estimates, A valuable tool for ergonomic evaluations", Professional Safety, pp. 18-24, (Oct. 2002).

Moondragon's Health Therapy Enemas: Phosphosoda Enema (Available online on Jan. 20, 2003 from the web archive: http://web.archive.org./web/20030130063720/http://www.moondragon.org/health/therapy/phosphosodaenema.html). Retrieved from the internet on Jan. 14, 2009; 3 pages.

Remington's Pharmaceutical Sciences, Alfonso Gennaro Ed., 17 edition, Mack Publishing Co. Easton, PA., (1985).

Schmelzer et al., "Colonic Cleansing, Fluid Absorption, and Discomfort Following Tap Water and Soapsuds Enemas", Applied Nursing Research, vol. 13, No. 2, pp. 83-91. (2000).

Laxative Drug Products for Over-the-Counter Human Use; Tentaive Final Monograph, Department of Health and Human Services, Federal Register, 21 CFR Part 334, vol. 50 No. 10, pp. 2151-2158, (1985).

Thomas, R., et al, "Administering an Enema", Delmars Fundamental and Advanced Nursing Skills, Gaylene Altman, Cengage Learning, 3 pages, (2003).

Ficha Técnica, product description, Laboratorios Casen-Fleet, S.L., Spain, Copyright © 2005.

Prospecto, product description, Laboratorios Casen-Fleet, S.L., Spain, Copyright © 2005.

Chemical Description of: "Bisacodyl", The Merck Index Fourteenth Edition, p. 205, (2006).

Ficha Tecnica Enema Casen, (2004) with English translation.

Physicians' Desk Reference, Product Information for Fleet Enema, pp. 896, (1981).

* cited by examiner

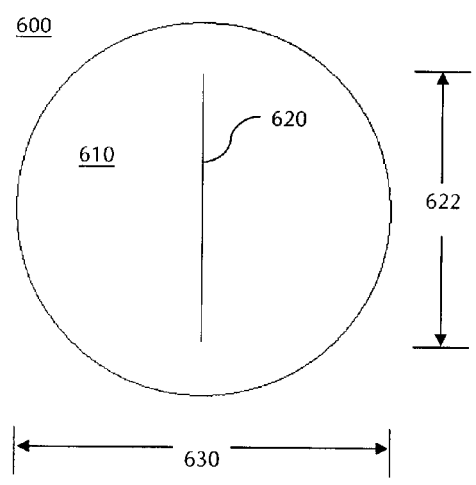
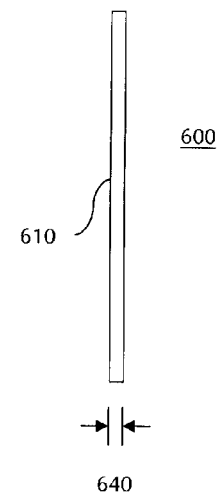
FIG. 6A                                  FIG. 6B

ENEMA DISPENSER

CROSS REFERENCE TO RELATED APPLICATION

This application is a continuation application of U.S. application Ser. No. 11/152,818, filed Jun. 14, 2005, entitled "ENEMA DISPENSER," now U.S. Pat. No. 8,147,445.

BACKGROUND

Bowel cleansing procedures typically involve the purging of the colon using an enema. An enema may be packaged as an over-the-counter therapeutic product for use by a consumer. Such a ready-to-use enema includes a liquid in a dispenser, which is typically a flexible bottle equipped with a nozzle. The liquid is administered by inserting the nozzle into the rectum of the patient, and squeezing the bottle to force the liquid through the nozzle and into the patient's colon.

The force required to squeeze the liquid from an enema dispenser affects the ease with which a user may administer the liquid. The self-administration of a conventional enema may be especially difficult for elderly patients, due to the squeeze force required to deliver a complete dose of the enema liquid. Although it would be advantageous to decrease the amount of squeeze force required to administer an enema, such a modification may adversely affect other desirable features of the product. In particular, it is desirable to prevent any reflux of liquid back into the bottle after the enema liquid has been delivered, and it is desirable to prevent leakage of the enema liquid from the dispenser prior to use. A simple reduction in the resistance to flow of the liquid through the dispenser may compromise these features.

It is desirable to provide an enema that is easier to administer, and that prevents reflux of liquid into the bottle after use and leakage of the enema liquid prior to use. It is also desirable to provide enema dispensers that can be used to more easily administer a variety of different enema liquids. It is also desirable to provide enema dispensers that can be used to more easily administer a range of doses of enema liquids.

SUMMARY

In one aspect, the invention provides a valve including a membrane having a slit and a thickness from 0.05 to 0.90 millimeter (mm).

In yet another aspect, the invention provides a nozzle including a proximal opening, a distal opening, and a lumen between the proximal opening and the distal opening; and a valve, as described above, attached to the nozzle and extending across the lumen.

In yet another aspect, the invention provides a dispenser including a bottle having a bottle opening; a nozzle, attached to the bottle at the bottle opening; and a valve, as described above. The nozzle includes a proximal opening, a distal opening, and a lumen between the proximal opening and the distal opening.

In yet another aspect, the invention provides an enema including a bottle having a bottle opening; a nozzle, attached to the bottle at the bottle opening; a liquid in the bottle; and a valve, as described above. The nozzle includes a proximal opening, a distal opening, and a lumen between the proximal opening and the distal opening;

In yet another aspect, the invention provides an enema including a bottle having a bottle opening; a nozzle, attached to the bottle at the bottle opening and having a distal opening; and a liquid in the bottle. At least a portion of the liquid can be dispensed through the distal opening when the bottle is compressed with a force of at most 15 Newtons.

In yet another aspect, the invention provides an enema including a bottle having a bottle opening; a nozzle, attached to the bottle at the bottle opening and having a distal opening; and at least a unit dose of a liquid in the bottle. At least 50% of the unit dose can be dispensed through the distal opening when the bottle is compressed with a force of at most 60 Newtons.

In yet another aspect, the invention provides an enema including a means for containing a liquid; a means for delivering at least a unit dose of the liquid to a colon; a means for preventing flow of the liquid from the containing means to the colon until a compression force of at most 15 Newtons is applied to the containing means; and a means for preventing liquid flow from the colon into the containing means.

In yet another aspect, the invention provides method of bowel cleansing including inserting an enema as described above into a rectum, and applying a compression force to the bottle.

The following definitions are included to provide a clear and consistent understanding of the specification and claims.

The term "membrane" means a flexible sheet of material having a thickness dimension less than 10% of its width or length dimensions.

The term "proximal," with respect to an enema and/or its components, means a position or direction that would be away from the body of the patient when the enema is administered.

The term "distal," with respect to an enema and/or its components, means a position or direction that would be toward or inside the body of the patient when the enema is administered.

The term "lumen" means a passageway through which liquid may flow.

The term "squeeze force" means the compression force required to squeeze a particular volume of liquid from a dispenser through a distal opening of the dispenser.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 6A is a top representation of a valve, and FIG. 6B is a side representation of the valve.

DETAILED DESCRIPTION

The present invention provides an enema that can be administered with a lower amount of force. The enema includes a liquid in a dispenser having a bottle, a nozzle attached to the bottle, and a valve. The valve may be a membrane having a slit and a thickness of at most 0.90 millimeter (mm). The valve may be attached to the bottle or may be attached to the nozzle. The present invention also includes a method of bowel cleansing, including inserting the enema into a rectum and applying a compression force to the enema bottle.

It has been surprisingly found that a valve having a thickness less than the conventional thickness may provide for a reduction in the squeeze force required to dispense a liquid from an enema dispenser. Although the liquid may experience a lower resistance to flow during administration, there may be little or no increase in reflux of liquid back into the enema bottle after the enema liquid has been administered. In addition, there may be little or no increase in leakage of the enema liquid prior to administration. The dispenser design may provide these advantageous properties for a variety of enema liquids and for a range of doses of these liquids.

Figure 1:
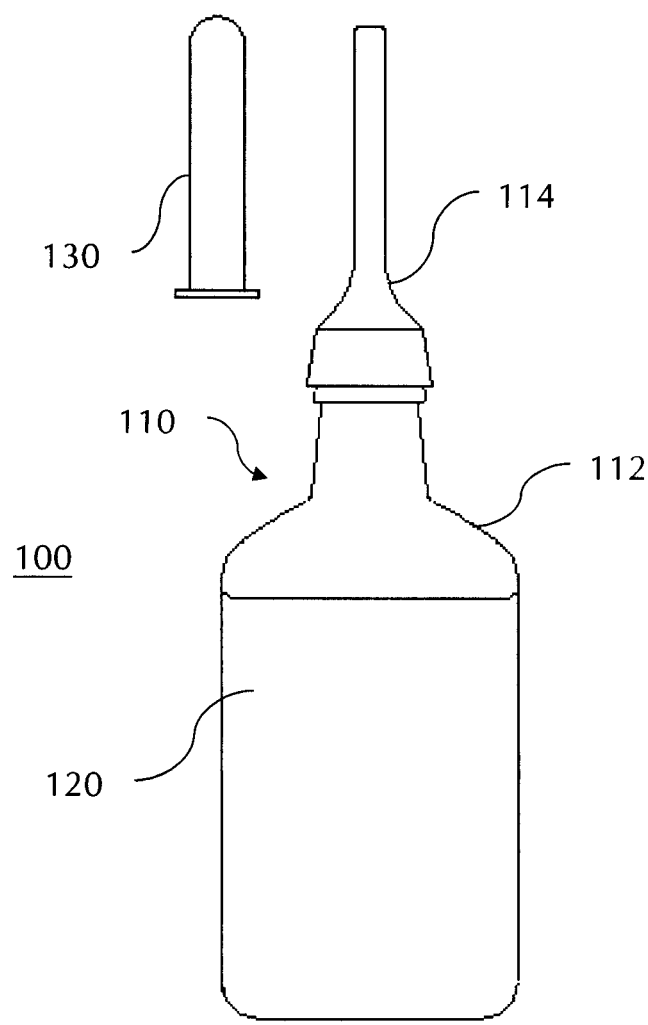
FIG. 1 is a side representation of an enema.

FIG. 1 represents an enema 100 including an enema dispenser 110, an enema liquid 120 in the dispenser, and optional shield 130. The dispenser 110 includes a bottle 112 and a nozzle 114. The bottle 112 may have a variety of shapes and sizes, and preferably contains a unit dose of the enema liquid 120. The nozzle 114 is attached to the bottle 112 at the opening of the bottle, and includes a passageway for the enema liquid. At least a portion of the exterior of the nozzle 114 may have a lubricant to facilitate proper insertion of the nozzle into the patient. The shield 130 fits over the nozzle 114, protecting the nozzle and/or sealing the dispenser prior to use. The shield may help maintain a lubricant in place on the nozzle prior to use.

The enema liquid 120 may be any liquid that promotes a bowel movement when introduced into the colon. Examples of enema liquids include water; hypertonic aqueous salt solutions; solutions or suspensions of cathartic agents, such as bisacodyl or phenolphthalein; and mineral oil. Preferably a unit dose of the enema liquid 120 is present in the bottle 112 of the dispenser 110. The volume of the unit dose depends on the type of enema liquid, the specific formulation of active and inactive ingredients in the liquid, and the type of patient for which the enema is intended. Preferably the total volume of the enema liquid 120 in the bottle 112 is greater than the volume of the unit dose, since a small amount of the liquid typically remains in the bottle after the enema has been administered to the patient.

In one example, the enema liquid 120 is a hypertonic aqueous salt solution containing water, dibasic sodium phosphate ($Na_2HPO_4$) and monobasic sodium phosphate ($NaH_2PO_4$). An enema containing this type of composition is referred to as a "saline enema." Typical amounts of these ingredients for unit dose administrations to adults are from 6.84 to 7.56 grams dibasic sodium phosphate and from 18.24 to 20.16 grams monobasic sodium phosphate. The concentration of the dibasic sodium phosphate may be from 0.02 to 0.10 grams per milliliter (g/mL), and the concentration of the monobasic sodium phosphate may be from 0.10 to 0.25 g/mL. In a typical phosphate enema liquid formulation, the concentration of the dibasic sodium phosphate may be from 0.04 to 0.08 g/mL, and the concentration of the monobasic sodium phosphate may be from 0.12 to 0.20 g/mL. Preferably the concentration of the dibasic sodium phosphate is from 0.05 to 0.07 g/mL, and the concentration of the monobasic sodium phosphate is from 0.14 to 0.18 g/mL. For enemas based on this typical formulation, the unit dose for an adult may be from 85 to 130 mL, and the total liquid volume may be from 100 to 150 mL. For enemas based on this typical formulation, the unit dose for a child may be from 45 to 65 mL, and the total liquid volume may be from 50 to 75 mL. Typical amounts of these ingredients for unit dose administrations to children are from 3.42 to 3.78 grams dibasic sodium phosphate, and from 9.12 to 10.08 grams monobasic sodium phosphate.

In another phosphate enema liquid formulation, the concentration of the dibasic sodium phosphate may be from 0.01 to 0.05 g/mL, and the concentration of the monobasic sodium phosphate may be from 0.05 to 0.12 g/mL. This formulation range is disclosed in co-pending U.S. patent application Ser. No. 10/846,488, filed May 13, 2004, entitled "Large Volume Enema." In the large volume phosphate enema liquid formulation, the concentration of the dibasic sodium phosphate preferably is from 0.03 to 0.04 g/mL, and the concentration of the monobasic sodium phosphate preferably is from 0.07 to 0.09 g/mL. For enemas based on this formulation, the unit dose for an adult may be from 170 to 260 mL, and the total liquid volume may be from 200 to 300 mL.

In another example, the enema liquid 120 is an aqueous suspension of 4,4'-(2-pyridylmethylene)bisphenol diacetate (bisacodyl). The concentration of bisacodyl may be from 0.05 to 0.1 milligrams per milliliter (mg/mL), and preferably is from 0.2 to 0.4 mg/mL. For bisacodyl enemas based on this formulation, the unit dose for an adult may be from 25 to 35 mL, and the total liquid volume may be from 30 to 45 mL.

In another example, the enema liquid 120 is mineral oil. For mineral oil enemas, the unit dose for an adult may be from 85 to 130 mL, and the total liquid volume may be from 100 to 150 mL.

Figure 2:
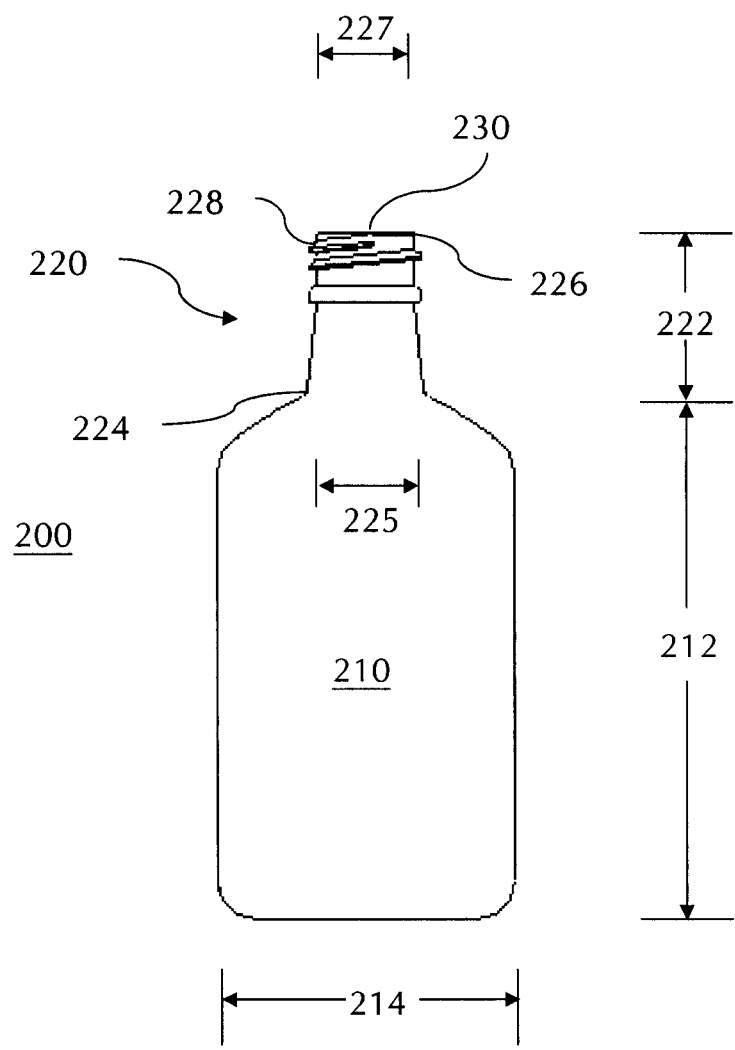
FIG. 2 is a side representation of a bottle.

FIG. 2 represents a bottle 200 including a body 210, a neck 220 and an opening 230. The body 210 has a length 212 and a width 214. The neck 220 has a length 222, a proximal end 224 at the junction with the body 210, a distal end 226 at the opening 230, and optional screw threads 228. The proximal end 224 of the neck has a width 225, and the distal end 226 of the neck has a width 227. The length 212 may be from 4 to 12 centimeters (cm), and the width 214 may be from 2.5 to 6 cm. The length 222 may be from 2 to 5 cm, the width 225 may be from 1 to 3 cm, and the width 227 may be from 0.7 to 2.5 cm. The width 227 corresponds to the diameter of opening 230.

The bottle 200 preferably is a flexible material. Examples of flexible materials for the bottle 200 include polyethylene, polypropylene, polyisoprene, polybutadiene, ethylene-propylene-diene copolymers (EPDM), styrene-butadiene copolymers (SBR), butadiene-acrylonitrile copolymers (NBR, or Buna-N), neoprene elastomer (polychloroprene and its copolymers), polyurethane elastomer, and silicone elastomer. Examples of flexible polyethylenes include LDPE, LLDPE and HDPE. Preferably the flexible material is latex-free and sterile. It may be desirable for the bottle to be transparent or translucent, permitting the liquid contents to be viewed. It may be desirable for the bottle to contain printed information, such as brand information, instructions for use, and/or an expiration date.

The opening 230 and the area of the neck 220 near the opening preferably are sized and shaped to provide a liquid-tight seal with a nozzle, such as nozzle 114 in FIG. 1. Optional screw threads 228 may coordinate with screw threads inside the nozzle to secure the nozzle to the opening 230. It may be desirable for the opening 230 and the area of the neck 220 near the opening to be configured uniformly for bottles that otherwise may have a variety of shapes and sizes. Such a uniform configuration may provide for a single type of nozzle to be used with a variety of different bottles.

Figure 3:
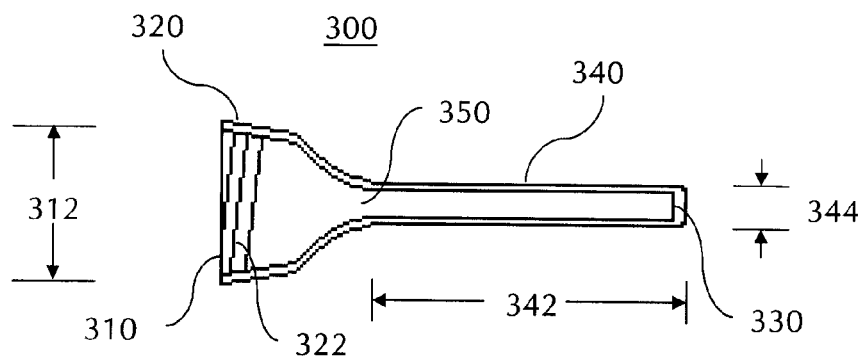
FIG. 3 is a side cross section representation of a nozzle.

FIG. 3 represents a cross sectional view of a nozzle 300 including a proximal opening 310 having a width 312, an attachment region 320 including optional screw threads 322, a distal opening 330, a tip region 340 having a length 342 and a width 344, and a lumen 350. The proximal opening 310 and the attachment region 320 preferably are sized and shaped to provide a liquid-tight seal with an opening of a bottle, such as opening 230 in FIG. 2. Optional screw threads 322 may coordinate with screw threads on a bottle to secure the nozzle to the bottle opening. The length 342 of the tip region 340 preferably is long enough to place the distal opening 330 within the colon of the patient. The length 342 may be from 3 to 5 cm. The width 344 of the tip region 340 preferably is small enough to provide insertion of the tip region through the rectum without discomfort to the patient. The width 344 preferably is smaller than the width 312 of the proximal opening. The width 344 may be from 0.3 to 1 cm. The lumen 350 is a passageway for displacement of a liquid from a bottle, such as bottle 200 in FIG. 2, through the distal opening 330 of the nozzle. The nozzle 300 may be all one piece, or it may contain two or more pieces.

Figure 4:
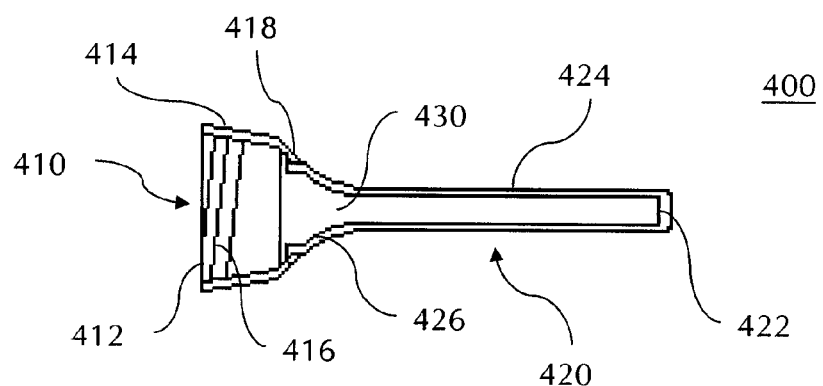
FIG. 4 is a side cross section representation of a nozzle containing two pieces.

FIG. 4 represents a cross sectional view of a nozzle 400 including a collar 410 and an extension 420 as two separate pieces that together form a lumen 430. The collar 410 includes a proximal opening 412, an attachment region 414 having optional screw threads 416, and a tapered end 418. The extension 420 includes a distal opening 422, a tip region 424, and a flared end 426. The tapered end 418 and the flared end 426 preferably fit together to form a liquid-tight seal.

Figure 5:
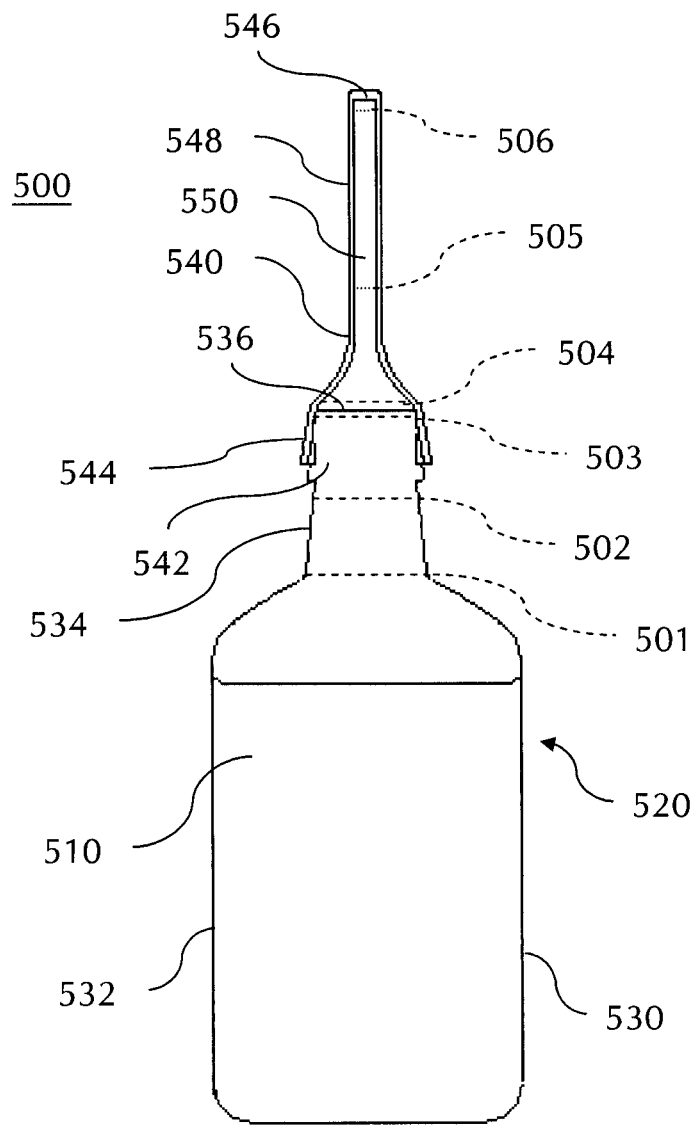
FIG. 5 is a side cross section representation of an enema.

FIG. 5 represents a cross sectional view of an enema 500 including an enema liquid 510 and a dispenser 520, and illustrating possible positions 501-506 of a valve within the dispenser. The dispenser 520 includes a bottle 530 and a nozzle 540. The bottle 530 includes a body 532, a neck 534 and an opening 536. The nozzle 540 includes a proximal opening 542, an attachment region 544, a distal opening 546, a tip region 548 and a lumen 550. A valve may be positioned at any point along the dispenser 520 beyond the level of liquid 510. A valve may be attached to the bottle 530, such as at the junction 501 between the body 532 and the neck 534, at a point 502 within the neck, or at a point 503 at or near the opening 536. A valve may be attached to the nozzle 540, such as at a point 504 at or near the attachment region 544, at a point 505 within the tip region 548, or at a point 506 at or near the distal opening 546. In one example, a valve may be attached to the opening 536 of the bottle 530. In another example, a valve may be attached to the nozzle 540 such that the valve extends across the lumen 550.

An enema dispenser valve may be any object that inhibits flow of the liquid into or out of an enema dispenser. Referring to FIG. 5, the valve minimizes or prevents liquid flow from the bottle 530 through the distal opening 546 until a critical compression force is applied to the bottle 530. Once the critical compression force is applied, the enema liquid can flow through the valve and out of the dispenser. Preferably the critical compression force is greater than the forces typically encountered during normal handling of the enema prior to administration.

The valve also minimizes or prevents liquid flow from the surrounding environment into the dispenser, which may have the possibility of occurring after administration of the enema liquid to a patient. Referring to FIG. 5, for example, the valve minimizes or prevents liquid flow from the distal opening 546 back into the bottle 530. Without the valve, liquid might reflux back into the dispenser due to the pressure of the liquid in contact with the exterior of the dispenser and/or the vacuum created in the interior of the dispenser during the delivery of the enema liquid. Preferably the valve prevents the flow of liquid back into the dispenser for combinations of external liquid pressure and internal vacuum pressure typically encountered during normal administration of the enema.

FIGS. 6A and 6B represent a valve 600 including a membrane 610 having a slit 620 of a length 622, a diameter 630, and a thickness 640. The membrane 610 is a disc of flexible material. Examples of flexible materials for membrane 610 include polyisoprene, polybutadiene, ethylene-propylene-diene copolymers (EPDM), styrene-butadiene copolymers (SBR), butadiene-acrylonitrile copolymers (NBR, or Buna-N), neoprene elastomer (polychloroprene and its copolymers), polyurethane elastomer, and silicone elastomer. The flexibility of materials is quantified by the Shore A durometer value, which is measured according to ASTM D2240 00. The membrane may have a hardness of less than 150 Shore A, preferably less than 100 Shore A, and more preferably from 40 to 80 Shore A. Preferably the membrane is latex-free and sterile. For example, the membrane material may be sterilized by irradiation, by autoclave treatment, or by exposure to ethylene oxide.

The slit 620 of the valve 600 has two sides that remain in contact until a critical force is applied to the dispenser. When the two sides of the slit are in contact, liquid flow through the slit is minimized or prevented. Preferably the two sides of the slit form a liquid-tight seal when in contact. When a sufficient liquid pressure contacts the slit, the two sides may separate, allowing the liquid to flow through the valve. Preferably the slit permits liquid flow in only one direction, allowing flow from the dispenser when a critical force is applied, and preventing flow back into the dispenser. The length 622 of the slit is limited by the diameter 630 of the valve. For example, the length 622 may be from 10 to 90% of the diameter 630. Preferably the length 622 is from 40 to 80% of the diameter 630, and more preferably is from 50 to 70% of the diameter 630. For a diameter 630 of at most 3 cm, the length 622 preferably is from 0.1 to 2.5 cm, more preferably is from 0.7 to 2.0 cm, and more preferably is about 1.3 cm.

The diameter 630 of the valve 600 is related to the internal diameter of the dispenser at the location of the valve. For a valve positioned in the nozzle and in contact with the opening of the bottle, the diameter 630 may be from 0.5 to 3 cm, preferably is from 1.5 to 2.5 cm, and more preferably is about 2 cm.

The thickness 640 of the valve 600 may be at most 0.90 mm. Preferably the thickness 640 is from 0.05 to 0.90 mm. More preferably the thickness 640 is from 0.10 to 0.90 mm, more preferably is from 0.5 to 0.90 mm, more preferably is from 0.60 to 0.89 mm, and more preferably is from 0.70 to 0.80 mm.

Figure 7A:
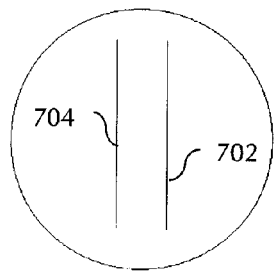
FIG. 7A-E are top representations of valves.
Figure 7B:
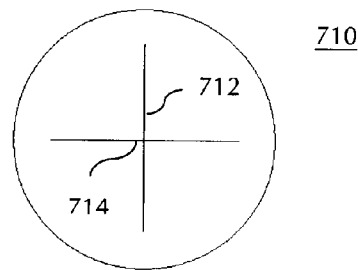
Figure 7C:
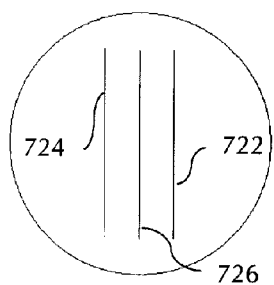
Figure 7D:
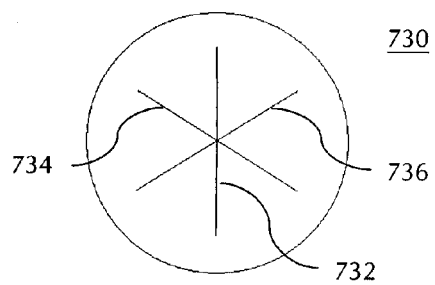
Figure 7E:
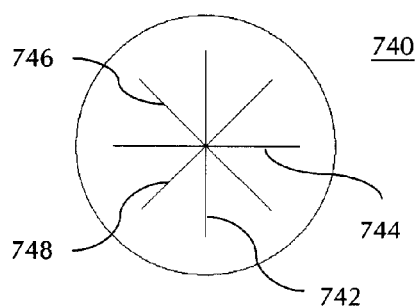

FIGS. 7A through 7E represent valves having different slit configurations. FIG. 7A represents valve 700 including two separate slits 702 and 704. FIG. 7B represents valve 710 including two intersecting slits 712 and 714. FIG. 7C represents valve 720 including three separate slits 722, 724 and 726. FIG. 7D represents valve 730 including three intersecting slits 732, 734 and 736. FIG. 7E represents valve 740 including four intersecting slits 742, 744, 746 and 748. Slits that do not intersect may be substantially parallel, or they may be oriented at an angle relative to each other.

A valve including a membrane, a slit, and a thickness of at most 0.90 mm may provide a reduction in the force required to dispense an enema liquid from an enema dispenser. This reduction in the force required to dispense an enema liquid from the dispenser may be quantified in terms of the squeeze force of the enema. Squeeze force is measured by the following test. An enema is placed horizontally in a holder secured to a base of a test stand. The holder is a longitudinal cross section of a hollow cylinder having a radius of curvature of 2 inches (5.08 cm), an arc of 130-degrees, a length of 5.875 inches (14.92 cm), and capped at a right angle at each end with a 130-degree section of a washer having an outer diameter of 2 inches (5.08 cm) and an inner diameter of 13/16 inch (2.06 cm). Examples of test stands include mechanical test stands, pneumatic test stands, motorized test stands, and digital test stands. Specific examples of test stands include those available from Chatillon® (AMTEK TCI Division, Largo, Fla.), Cole-Parmer® Instrument Company (Vernon Hills, Ill.), and Imada, Inc. (Northbrook, Ill.). The test stand is equipped with a force gauge connected to a movable crosshead, where the crosshead is a rigid half-cylinder having a length of 3.25 inches (8.26 cm), a diameter of 2 inches (5.08 cm), and a chamfer on each semicircular end of 0.125 inch (0.318 cm) by 45 degrees. Examples of force gauges include those that operate mechanically, electronically or electromechanically, and may include an analog or a digital display of the force measurement. The nozzle of the enema is attached to one end of a tube, with the other end placed in a graduated cylinder positioned below the holder. The crosshead is lowered at a rate of 2 inches per minute (5.08 cm/min) to contact and compress the enema. The force measurements from the force gauge are recorded at the initiation of flow and at particular displaced volumes as measured in the graduated cylinder.

The compression force applied to the enema may be measured at the initiation of liquid flow. The compression force may also be measured once particular liquid volumes or percentages of the liquid volume originally contained in the enema are displaced. If the squeeze force is expressed as the compression force at a total displaced liquid volume, the units for squeeze force include lb-f@ x oz., Newtons@ x mL, and dynes@ x mL, where "x" is the total volume of liquid displaced at the measured compression force. If the squeeze force is expressed as the compression force at a percentage of displaced liquid volume, the units for squeeze force include lb-f@ y %, Newtons@ y %, and dynes@ y %, where "y" is the volume of liquid displaced as a percentage of the total volume of liquid originally contained in the enema. Examples of volume percentages at which compression measurements may be taken include 0% (flow initiation), 10%, 25%, 50%, 75% and 100% of the liquid volume originally contained in the enema.

Figure 8:
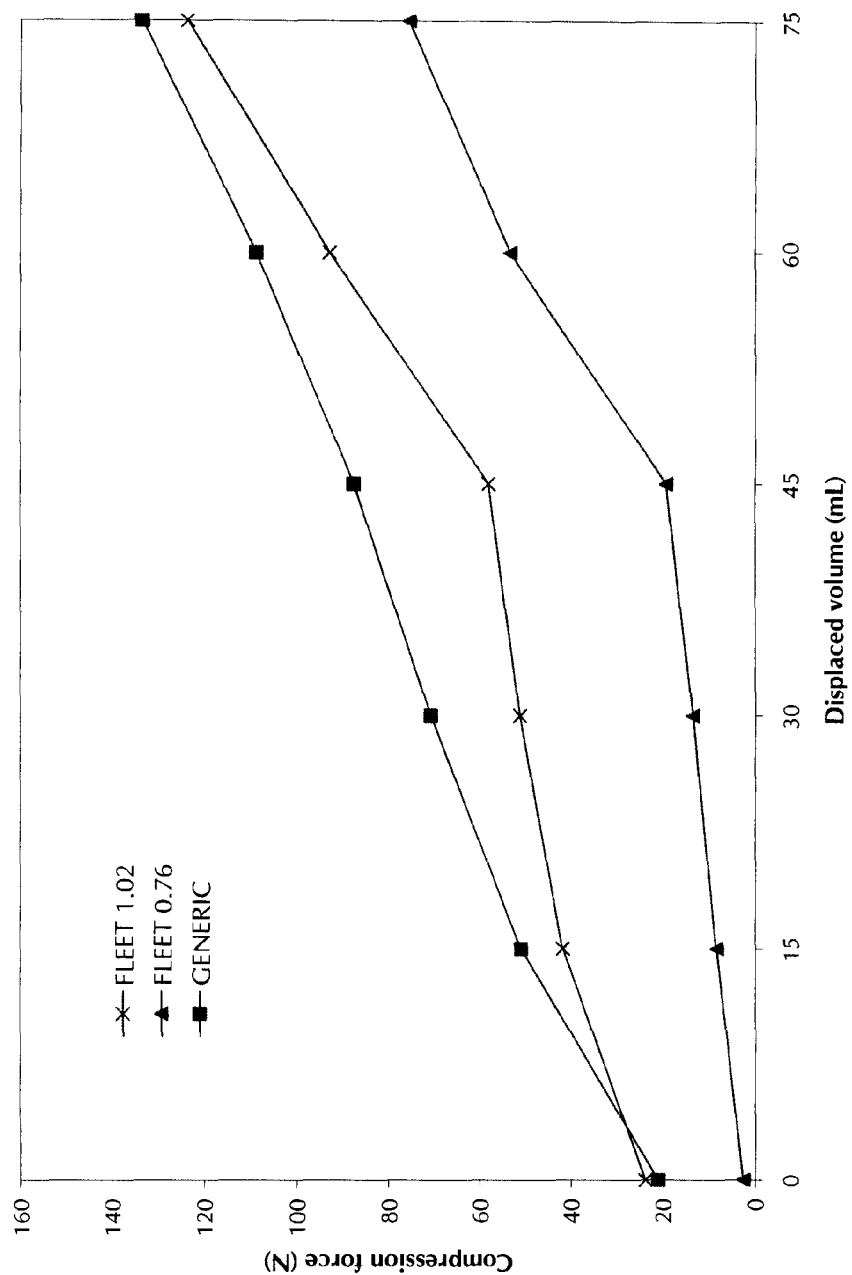
FIG. 8 is a graph of average squeeze force measurements for saline enemas for adult use (133 mL).

FIG. 8 is a graph of the average squeeze force measurements for saline enemas for adult use. These enemas contained a total volume of 133 mL, with a unit dose of 118 mL. Examples 1 and 2 below provide additional experimental details for these results. For the enemas made by the same manufacturer, enemas having a valve thickness of 0.76 mm (FLEET 0.76) showed a reduction in squeeze force at 75 mL of 39% relative to enemas having a valve thickness of 1.02 mm (FLEET 1.02). When compared to the other enemas made by different manufacturers and having a valve thickness of from 0.91-1.02 mm (GENERIC), the enemas having a valve thickness of 0.76 mm showed a reduction in squeeze force at 75 mL of 43%. At least 50% of the unit dose was delivered with a force of 53 Newtons (N) for the enemas having a valve thickness of 0.76 mm. In contrast, delivery of at least 50% of the unit dose of the enemas made by the same manufacturer and having a valve thickness of 1.02 mm required a force of 93 N, and delivery of at least 50% of the unit dose of the enemas made by different manufacturers required a force of 133 N. Liquid flow was initiated with a force of 2.6 N for the enemas having a valve thickness of 0.76 mm. In contrast, initiation of flow for the enemas made by the same manufacturer and having a valve thickness of 1.02 mm required a force of 24 N, and initiation of flow for the enemas made by different manufacturers required a force of 21 N.

Figure 9:
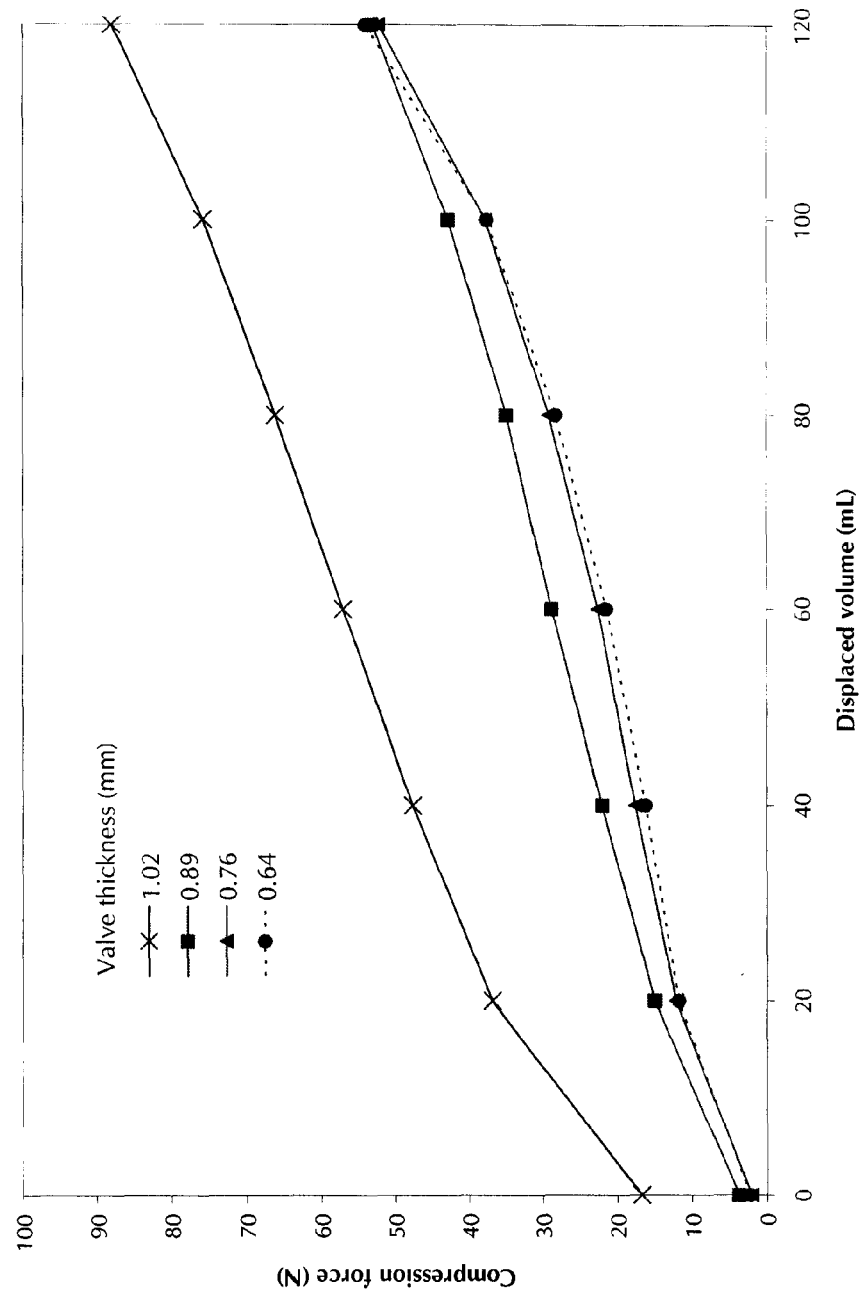
FIG. 9 is a graph of average squeeze force measurements for saline enemas for adult use (240 mL).

FIG. 9 is a graph of the average squeeze force measurements for large volume saline enemas for adult use. These enemas contained a total volume of 240 mL, with a unit dose of 190 mL. Examples 1 and 3 below provide additional experimental details for these results. Enemas having a valve thickness of 0.64, 0.76 or 0.89 mm showed a reduction in squeeze force at 120 mL of 39-41% relative to enemas having a valve thickness of 1.02 mm. At least 50% of the unit dose was delivered with a force from 38-43 N for the enemas having a valve thickness of 0.64-0.89 mm. In contrast, delivery of at least 50% of the unit dose of the enemas having a valve thickness of 1.02 mm required a force of 76 N. Liquid flow was initiated with a force of from 2-4 N for the enemas having a valve thickness of 0.64-0.89 mm. In contrast, initiation of flow for the enemas having a valve thickness of 1.02 mm required a force of 17 N.

Figure 10:
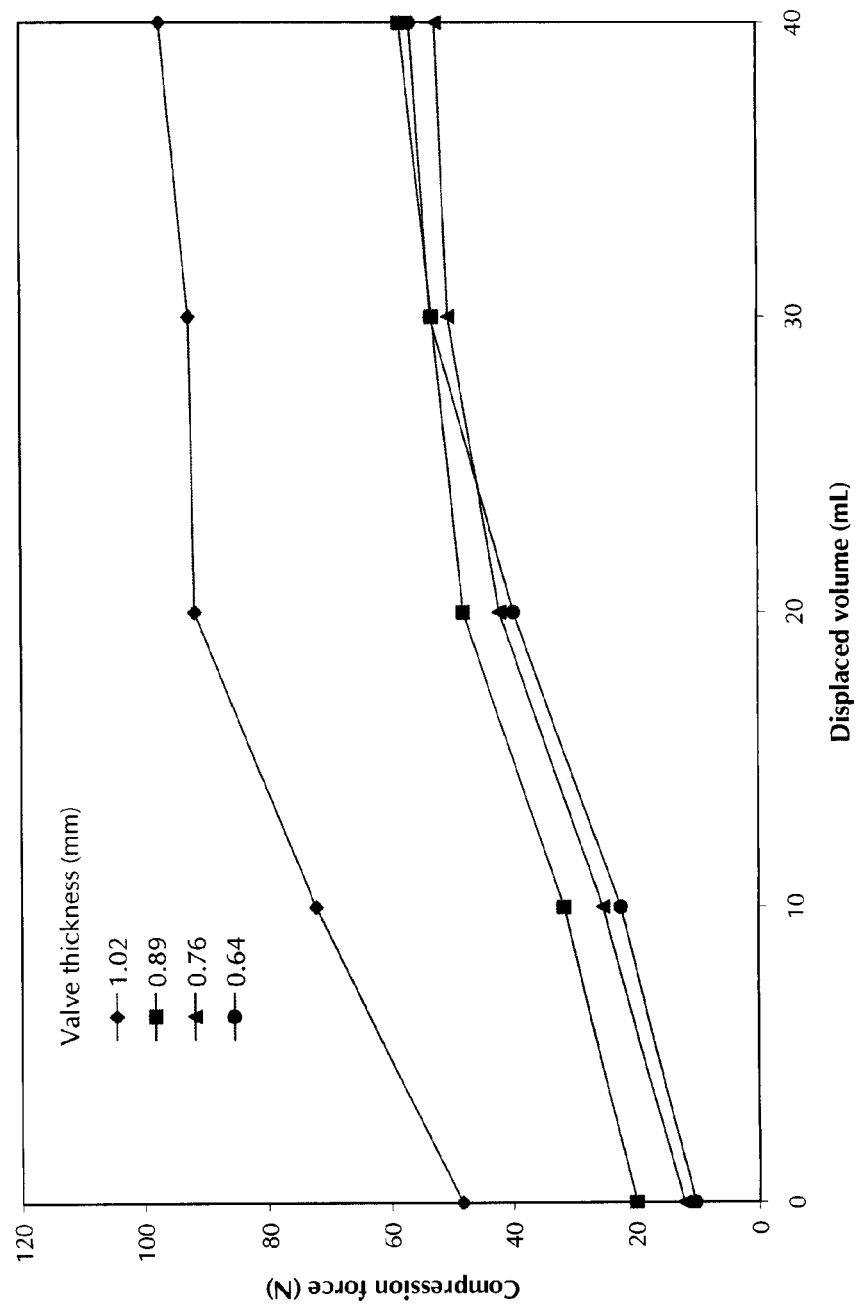
FIG. 10 is a graph of average squeeze force measurements for saline enemas for pediatric use (66 mL).

FIG. 10 is a graph of the average squeeze force measurements for saline enemas for pediatric use. These enemas contained a total volume of 66 mL, with a unit dose of 59 mL. Examples 1 and 4 below provide additional experimental details for these results. Enemas having a valve thickness of 0.64, 0.76 or 0.89 mm showed a reduction in squeeze force at 40 mL of 40-46% relative to enemas having a valve thickness of 1.02 mm. At least 50% of the unit dose was delivered with a force from 50-53 N for the enemas having a valve thickness of 0.64-0.89 mm. In contrast, delivery of at least 50% of the unit dose of the enemas having a valve thickness of 1.02 mm required a force of 93 N. Liquid flow was initiated with a force of from 10-20 N for the enemas having a valve thickness of 0.64-0.89 mm. In contrast, initiation of flow for the enemas having a valve thickness of 1.02 mm required a force of 48 N.

Figure 11:
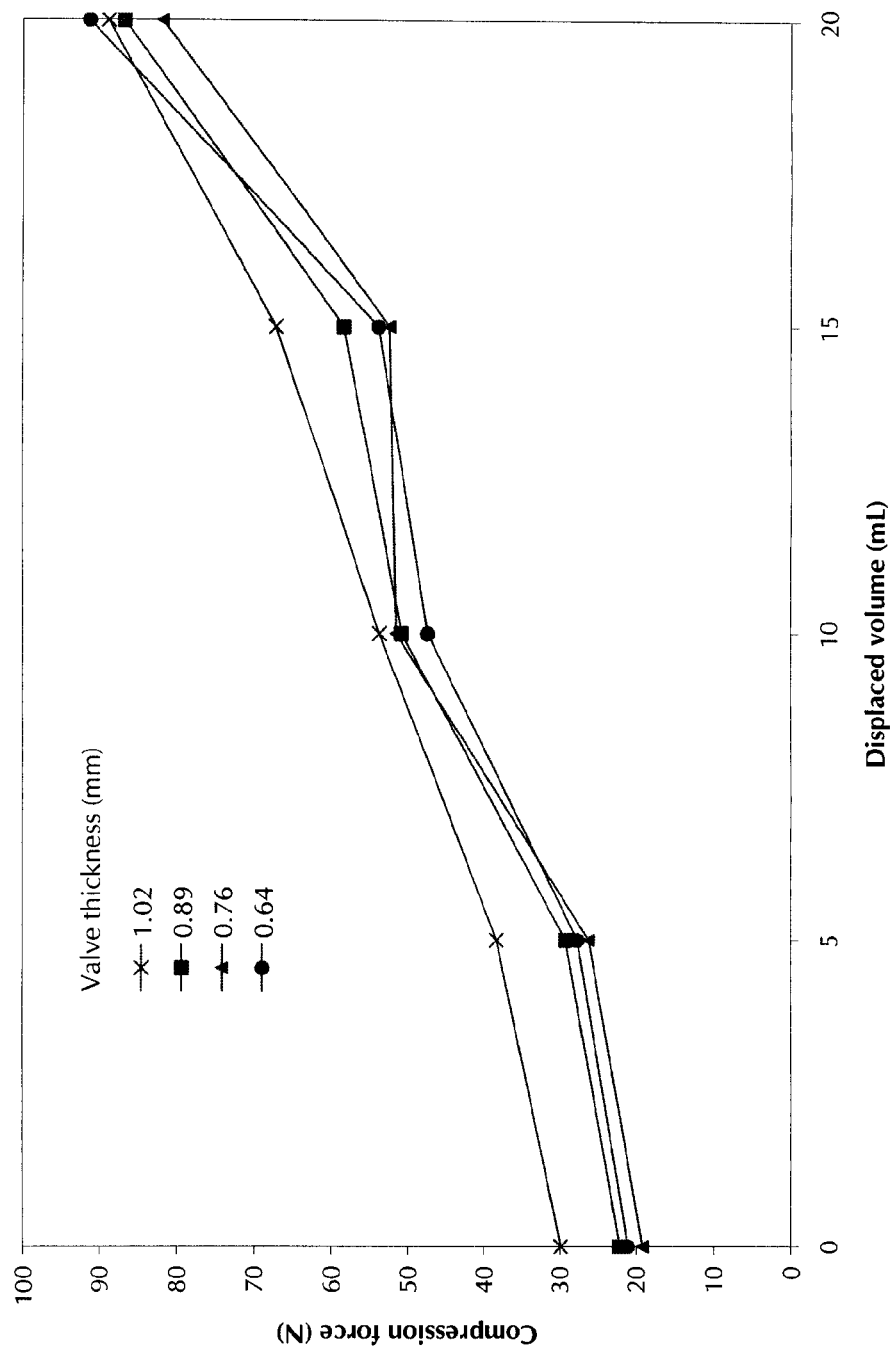
FIG. 11 is a graph of average squeeze force measurements for bisacodyl enemas for adult use.

FIG. 11 is a graph of the average squeeze force measurements for bisacodyl enemas for adult use. These enemas contained a total volume of 37 mL, with a unit dose of 30 mL. Examples 1 and 5 below provide additional experimental details for these results. Enemas having a valve thickness of 0.64, 0.76 or 0.89 mm showed squeeze force values that were approximately equivalent to or better than the squeeze force values for enemas having a valve thickness of 1.02 mm. In addition, the enemas having a valve thickness of 0.76 mm showed a reduction in squeeze force at all measured displaced volumes, relative to enemas having a valve thickness of 1.02 mm. At least 50% of the unit dose was delivered with a force from 52-58 N for the enemas having a valve thickness of 0.64-0.89 mm. In contrast, delivery of at least 50% of the unit dose of the enemas having a valve thickness of 1.02 mm required a force of 67 N.

Figure 12:
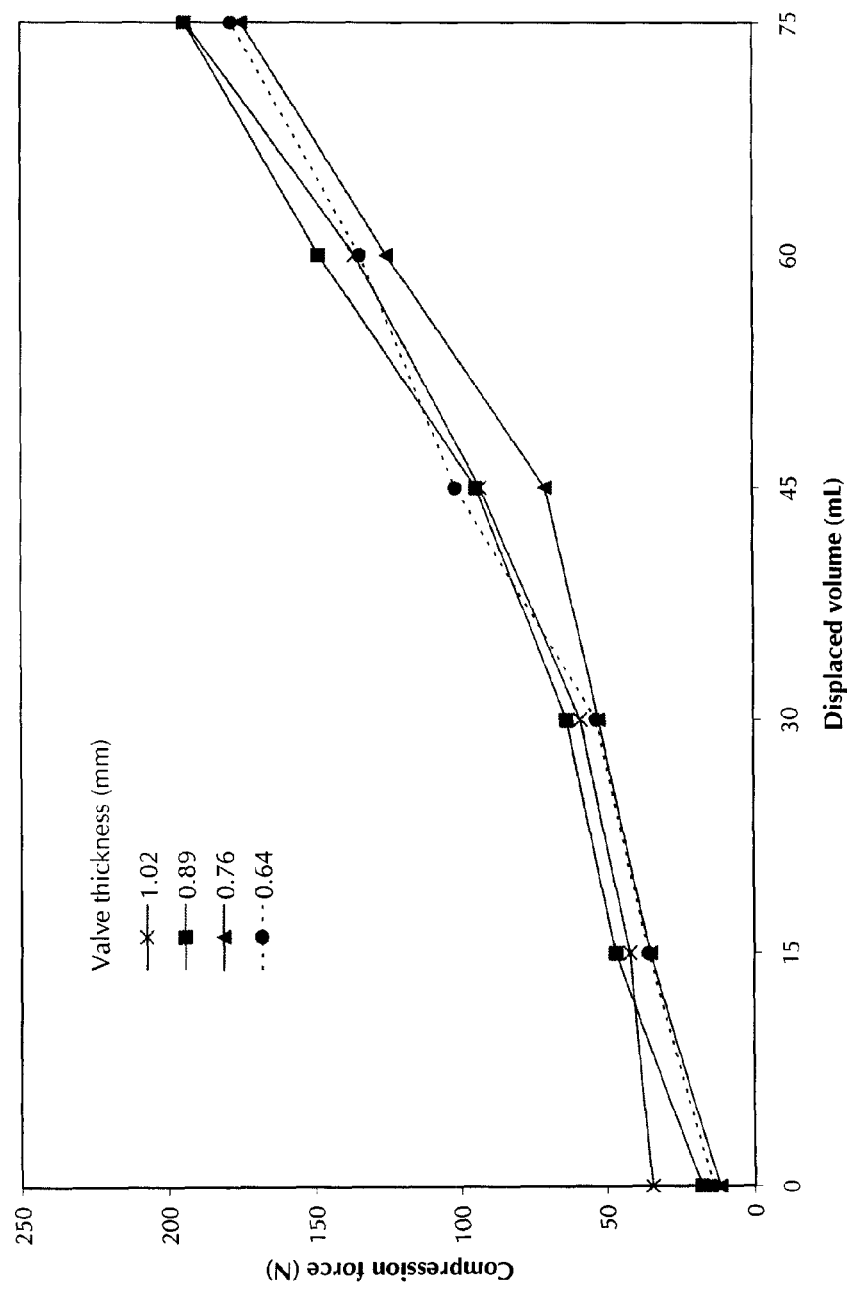
FIG. 12 is a graph of average squeeze force measurements for mineral oil enemas for adult use.

FIG. 12 is a graph of the average squeeze force measurements for mineral oil enemas for adult use. These enemas contained a total volume of 133 mL, with a unit dose of 118 mL. Examples 1 and 6 below provide additional experimental details for these results. Enemas having a valve thickness of 0.64, 0.76 or 0.89 mm showed squeeze force values that were approximately equivalent to or better than the squeeze force values for enemas having a valve thickness of 1.02 mm. In addition, the enemas having a valve thickness of 0.76 mm showed a reduction in squeeze force at all measured displaced volumes, relative to enemas having a valve thickness of 1.02 mm. Liquid flow was initiated with a force of from 12-18 N for the enemas having a valve thickness of 0.64-0.89 mm. In contrast, initiation of flow for the enemas having a valve thickness of 1.02 mm required a force of 35 N.

When incorporated into an enema dispenser, a valve including a membrane, a slit, and a thickness of at most 0.90 mm may provide a reduction in the force required to dispense an enema liquid from the dispenser. This effect may be greater for saline enemas. Within the saline enema system, the reduction in squeeze force was provided for enemas containing different dose sizes and/or containing different concentrations of the phosphate ingredients. A valve including a membrane having a slit and a thickness of from 0.70-0.80 mm may reduce the force required to administer a variety of enema liquids relative to an enema containing a conventional valve.

The advantageous reduction in squeeze force for an enema having a valve including a membrane, a slit, and a thickness of at most 0.90 mm may be provided without permitting reflux of liquid back into the dispenser after use. In addition, the advantageous reduction in squeeze force may be provided without permitting leakage of the liquid prior to use. It may be desirable for the thickness to be at least a minimum thickness, so as to ensure this prevention of reflux and leakage. Examples of minimum thicknesses include 0.05 mm, 0.10 mm, 0.60 mm and 0.70 mm.

The resistance of an enema dispenser to reflux of liquid back into the dispenser is measured by the following test. An enema is placed horizontally in a bath of water containing a dye, with the nozzle below the liquid surface. The enema bottle is squeezed by hand to expel a liquid volume corresponding to a unit dose of the enema liquid. The hand pressure is then released, with the nozzle maintained beneath the liquid surface, and the dispenser is observed for any colored water being drawn into the dispenser. The squeezing, releasing and observation steps are repeated four more times or until all liquid has been expelled from the dispenser.

Referring again to FIGS. 8 through 12, all of the enemas were tested for reflux, except for the "GENERIC" enemas. All of the enemas tested showed no evidence of reflux. Even though the thinner valves may have reduced the squeeze force of enemas, the valves did not permit reflux flow of liquid back into the enema dispenser. Thus, an improvement in enema squeeze force may be obtained without impairing the desirable reflux prevention characteristic.

Figure 13:
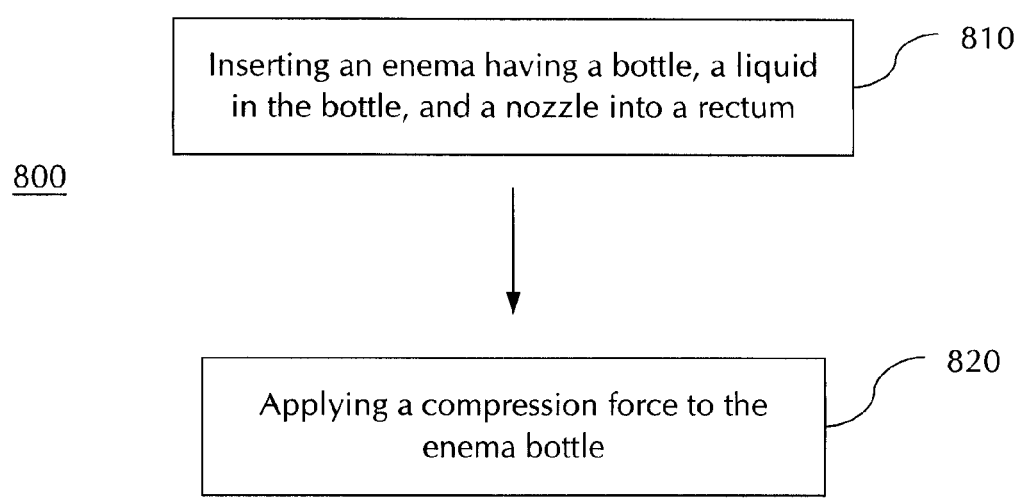
FIG. 13 represents a method of bowel cleansing.

FIG. 13 represents a method 800 of bowel cleansing, including inserting an enema having a bottle, a liquid in the bottle, and a nozzle into a rectum 810, and applying a compression force to the enema bottle 820. Referring to FIG. 1, the nozzle 114 of the enema dispenser 110 may be inserted into the rectum of a patient. The bottle 112 may then be compressed to displace the enema liquid 120 in the bottle through the nozzle 114 and into the colon of the patient. The compression of the bottle may be accomplished by squeezing the bottle by hand, either by the patient or by a separate user.

The following examples are provided to illustrate one or more preferred embodiments of the invention. Numerous variations may be made to the following examples that lie within the scope of the invention.

EXAMPLES

Example 1

Squeeze Force and Reflux Measurement Procedure

A Chatillon® UTSM-HS-FS test stand was equipped with a Chatillon® DFM-50 force gauge. The crosshead was an aluminum half-cylinder having a length of 3.25 inches (8.26 cm) and a diameter of 2 inches (5.08 cm). Each semicircular end had a chamfer of 0.125 inch (0.318 cm) by 45 degrees. The crosshead was attached to the test stand through a 10-32 hole in the center of the crosshead. The test stand was also equipped with a holder for a bottle. The holder was a longitudinal cross-section of a hollow stainless steel cylinder having an original diameter of 2 inches (5.08 cm). The arc of the partial cylinder was 130-degrees. The length of the holder was 5.875 inches (14.92 cm), and each end was connected to a 130-degree section of a stainless steel washer having an outer diameter of 2 inches (5.08 cm) and an inner diameter of $^{13}/_{16}$ inch (2.06 cm). The partial washers were at right angles to the partial cylinder wall. The holder was affixed to the base of the test stand by a 0.375 inch (0.953 cm) thick stainless steel adaptor plate having a length of 4.5 inches (11.43 cm) and a width of 3 inches (7.62 cm). The holder was centered on the plate and perpendicular with respect to the length of the plate. The plate had two ¼-20 holes, each positioned 0.5 inch (1.27 cm) from an end of the plate and centered 1.5 inches (3.81 cm) from each side of the plate. The plate was affixed to the base of the test stand by screws passing through each of these holes.

This apparatus was used to measure squeeze force of enemas. An enema was placed horizontally in the holder, and one end of a flexible tube was attached to the end of the enema nozzle. The other end of the flexible tube was placed in a graduated cylinder, which was positioned below the holder. The test stand was programmed to lower the crosshead at a rate of 2 inches per minute (5.08 cm/min). The force measurements were recorded at the initiation of flow and at particular displaced volumes as measured in the graduated cylinder.

The resistance of enemas to reflux was measured by the following procedure. An enema was placed horizontally in a bath of water containing a dye, with the nozzle below the liquid surface. The enema bottle was squeezed by hand to expel a liquid volume corresponding to a unit dose of the enema liquid. The hand pressure was then released, with the nozzle maintained beneath the liquid surface, and the dispenser was observed for any colored water being drawn into the dispenser. The squeezing, releasing and observation steps were repeated four more times or until all liquid had been expelled from the dispenser.

Example 2

Adult Saline Enemas

A series of saline enemas for adult use were examined using the procedures of Example 1. The saline enemas each contained 133 mL of an aqueous solution of dibasic sodium phosphate (0.06 g/mL) and monobasic sodium phosphate (0.16 g/mL). Of the 133 mL of total liquid, 118 mL is considered a unit dose. For the squeeze force testing, force measurements were recorded at the initiation of flow and at displaced volumes of 15 mL, 30 mL, 45 mL, 60 mL and 75 mL as measured in the graduated cylinder.

FLEET® saline enemas were equipped with membrane valves having a diameter of 0.778 inch (1.98 cm), a single slit having a length of 0.485 inch (1.23 cm), and a thickness either of 1.02 mm ("FLEET 1.02") or of 0.76 mm ("FLEET 0.76"). The membrane valves were made of a sterile elastomer having a hardness of from 66-76 Shore A. For these enemas, the squeeze force measurement was repeated for a total of 20 samples for each type of enema. Saline enemas from other manufacturers ("GENERIC") were equipped with membrane valves having a diameter of 0.778 inch (1.98 cm), a single slit having a length of 0.485 inch (1.23 cm), and a thickness from 0.91-1.02 mm. The squeeze force measurement was repeated for a total of 12 samples. FIG. 8 is a graph of the average squeeze force measurements for these enemas. One sample of each type of enema was also tested for reflux. No reflux was observed for any of the enemas tested.

Example 3

Large Volume Adult Saline Enemas

A series of FLEET® large volume saline enemas for adult use were equipped with membrane valves having a diameter of 1.98 cm, a single slit having a length of 1.23 cm, and a thickness of 1.02, 0.89, 0.76 or 0.64 mm. The membrane valves were made of a sterile elastomer having a hardness of from 66-76 Shore A. Each enema contained 240 mL of an aqueous solution of dibasic sodium phosphate (0.03 g/mL) and monobasic sodium phosphate (0.8 g/mL). Of the 240 mL of total liquid, 190 mL is considered a unit dose. These enemas were tested for squeeze force by the procedure of Example 1, with force measurements recorded at the initiation of flow and at displaced volumes of 20 mL, 40 mL, 60 mL, 80 mL, 100 mL and 120 mL as measured in the graduated cylinder. The squeeze force measurement was repeated for a total of 20 samples for each type of enema. FIG. 9 is a graph of the average squeeze force measurements for these enemas. One sample of each type of enema was also tested for reflux. No reflux was observed for any of the enemas tested.

Example 4

Pediatric Adult Saline Enemas

A series of FLEET® saline enemas for pediatric use were equipped with membrane valves having a diameter of 1.98 cm, a single slit having a length of 1.23 cm, and a thickness of 1.02, 0.89, 0.76 or 0.64 mm. The membrane valves were made of a sterile elastomer having a hardness of from 66-76 Shore A. Each enema contained 66 mL of an aqueous solution of dibasic sodium phosphate (0.06 g/mL) and monobasic sodium phosphate (0.16 g/mL). Of the 66 mL of total liquid, 59 mL is considered a unit dose. These enemas were tested for squeeze force by the procedure of Example 1, with force measurements recorded at the initiation of flow and at displaced volumes of 10 mL, 20 mL, 30 mL and 40 mL as measured in the graduated cylinder. The squeeze force measurement was repeated for a total of 3 samples for each type of enema. FIG. 10 is a graph of the average squeeze force measurements for these enemas. One sample of each type of enema was also tested for reflux. No reflux was observed for any of the enemas tested.

Example 5

Adult Bisacodyl Enemas

A series of FLEET® bisacodyl enemas for adult use were equipped with membrane valves having a diameter of 1.98 cm, a single slit having a length of 1.23 cm, and a thickness of 1.02, 0.89, 0.76 or 0.64 mm. The membrane valves were made of a sterile elastomer having a hardness of from 66-76 Shore A. Each enema contained 37 mL of an aqueous suspension of bisacodyl (0.33 mg/mL), and of the 37 mL of total liquid, 30 mL is considered a unit dose. These enemas were tested for squeeze force by the procedure of Example 1, with force measurements recorded at the initiation of flow and at displaced volumes of 5 mL, 10 mL, 15 mL and 20 mL as measured in the graduated cylinder. The squeeze force measurement was repeated for a total of 3 samples for each type of enema. FIG. 11 is a graph of the average squeeze force measurements for these enemas. One sample of each type of enema was also tested for reflux. No reflux was observed for any of the enemas tested.

Example 6

Adult Mineral Oil Enemas

A series of FLEET® mineral oil enemas for adult use were equipped with membrane valves having a diameter of 1.98 cm, a single slit having a length of 1.23 cm, and a thickness of 1.02, 0.89, 0.76 or 0.64 mm. The membrane valves were made of a sterile elastomer having a hardness of from 66-76 Shore A. Each enema contained 133 mL of total liquid, of which 118 mL is considered a unit dose. These enemas were tested for squeeze force by the procedure of Example 1, with force measurements recorded at the initiation of flow and at displaced volumes of 15 mL, 30 mL, 45 mL, 60 mL and 75 mL as measured in the graduated cylinder. The squeeze force measurement was repeated for a total of 3 samples for each type of enema. FIG. 12 is a graph of the average squeeze force measurements for these enemas. One sample of each type of enema was also tested for reflux. No reflux was observed for any of the enemas tested.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:
1. An enema, comprising:
a bottle comprising a bottle opening;
a nozzle, attached to the bottle at the bottle opening, and comprising a distal opening;
a valve comprising a single slit, attached to the nozzle;
a protective shield on the nozzle;
a liquid in the bottle;
wherein at least a portion of the liquid can be dispensed through the distal opening when the bottle is compressed with a force of at most 15 Newtons;
the valve is sterile, and
the valve has a thickness from 0.05 to 0.90 mm.
2. The enema of claim 1, wherein at least a portion of the liquid can be dispensed through the distal opening when the bottle is compressed with a force of at most 10 Newtons.
3. The enema of claim 1, wherein at least a portion of the liquid can be dispensed through the distal opening when the bottle is compressed with a force of at most 5 Newtons.
4. The enema of claim 1, wherein the liquid comprises a unit dose of an aqueous mixture comprising dibasic sodium phosphate and monobasic sodium phosphate.
5. The enema of claim 4, wherein the unit dose comprises from 6.84 to 7.56 grams dibasic sodium phosphate and from 18.24 to 20.16 grams monobasic sodium phosphate.
6. The enema of claim 5, wherein at least 50% of the unit dose can be dispensed from the distal opening when the bottle is compressed with a force of at most 80 Newtons.
7. The enema of claim 5, wherein at least 50% of the unit dose can be dispensed from the distal opening when the bottle is compressed with a force of at most 60 Newtons.

8. The enema of claim 5, wherein at least 50% of the unit dose can be dispensed from the distal opening when the bottle is compressed with a force of at most 40 Newtons.

9. The enema of claim 4, wherein the unit dose comprises from 3.42 to 3.78 grams dibasic sodium phosphate and from 9.12 to 10.08 grams monobasic sodium phosphate.

10. The enema of claim 9, wherein at least 50% of the unit dose can be dispensed from the distal opening when the bottle is compressed with a force of at most 80 Newtons.

11. The enema of claim 9, wherein at least 50% of the unit dose can be dispensed from the distal opening when the bottle is compressed with a force of at most 60 Newtons.

12. The enema of claim 1, wherein the liquid comprises a unit dose of mineral oil.

13. The enema of claim 12, wherein at least 50% of the unit dose can be dispensed from the distal opening when the bottle is compressed with a force of at most 80 Newtons.

14. The enema of claim 1, wherein liquid flow from the distal opening into the bottle is prevented.

15. The enema of claim 1, wherein the bottle comprises a flexible material; and wherein the flexible material is sterile.

16. An enema, comprising:
    a bottle comprising a bottle opening;
    a nozzle, attached to the bottle at the bottle opening, and comprising a distal opening;
    a valve comprising a single slit, attached to the nozzle;
    a protective shield on the nozzle;
    at least a unit dose of a liquid, in the bottle;
    wherein at least 50% of the unit dose can be dispensed through the distal opening when the bottle is compressed with a force of at most 60 Newtons;
    the valve is sterile, and
    the valve has a thickness from 0.05 to 0.90 mm.

17. The enema of claim 16, wherein at least 50% of the unit dose can be dispensed from the distal opening upon application of a compression force to the bottle of at most 55 Newtons.

18. The enema of claim 16, wherein at least 50% of the unit dose can be dispensed from the distal opening upon application of a compression force to the bottle of at most 40 Newtons.

19. The enema of claim 16, wherein the liquid comprises a composition selected from the group consisting of an aqueous mixture comprising dibasic sodium phosphate and monobasic sodium phosphate, and an aqueous mixture comprising bisacodyl.

20. The enema of claim 16, wherein liquid flow from the distal opening into the bottle is prevented.

21. The enema of claim 16, wherein the bottle comprises a flexible material; and wherein the flexible material is sterile.

* * * * *